US012642882B2

(12) United States Patent
Tajdaran et al.

(10) Patent No.: US 12,642,882 B2
(45) Date of Patent: ***Jun. 2, 2026

(54) DRUG DELIVERY SYSTEM AND METHODS OF USING THE SAME

(71) Applicant: Axogen Corporation, Alachua, FL (US)

(72) Inventors: Kasra Tajdaran, Alachua, FL (US); Xeve Silver, Alachua, FL (US); Robert C. Diluccio, Alachua, FL (US)

(73) Assignee: Axogen Corporation, Alachua, FL (US)

( * ) Notice: Subject to any disclaimer, the term of this patent is extended or adjusted under 35 U.S.C. 154(b) by 646 days.

This patent is subject to a terminal disclaimer.

(21) Appl. No.: 18/068,791

(22) Filed: Dec. 20, 2022

(65) Prior Publication Data

US 2023/0190990 A1      Jun. 22, 2023

Related U.S. Application Data

(60) Provisional application No. 63/265,861, filed on Dec. 22, 2021.

(51) Int. Cl.
*A61L 17/12*      (2006.01)
*A61B 17/06*      (2006.01)

(52) U.S. Cl.
CPC ........ *A61L 17/12* (2013.01); *A61B 17/06166* (2013.01)

(58) Field of Classification Search
CPC .......................... A61L 17/12; A61B 17/06166
See application file for complete search history.

(56)      References Cited

U.S. PATENT DOCUMENTS

| | | | | |
|---|---|---|---|---|
| 2003/0211135 A1* | 11/2003 | Greenhalgh | .............. | A61F 2/07 424/443 |
| 2012/0221025 A1 | 8/2012 | Simpson et al. | | |
| 2017/0258901 A1 | 9/2017 | Bushman | | |
| 2022/0054714 A1 | 2/2022 | Davis et al. | | |

FOREIGN PATENT DOCUMENTS

| | | | | |
|---|---|---|---|---|
| CN | 106902389 A | 6/2017 | | |
| CN | 109498839 A | 3/2019 | | |
| WO | WO-2020150226 A1 * | 7/2020 | .............. | A61P 25/00 |
| WO | WO-2020206128 A1 * | 10/2020 | ........... | A61K 40/428 |

OTHER PUBLICATIONS

International Search Report and Written Opinion of International Application No. PCT/US2023/084741, mailed on Apr. 24, 2024 (9 pages).

(Continued)

*Primary Examiner* — Blessing M Fubara
(74) *Attorney, Agent, or Firm* — Bookoff McAndrews, PLLC

(57)      ABSTRACT

A method of preparing an implantable biomaterial includes combining a polymer with a neuro-regenerative agent or immunosuppressive agent selected from a group comprising at least one of: rapamycin, cyclosporine A, or analogs thereof, melting the polymer, and extruding the polymer and the neuro-regenerative agent or immunosuppressive agent to form the implantable biomaterial.

21 Claims, 4 Drawing Sheets

100

(56)            References Cited

OTHER PUBLICATIONS

International Search Report and Written Opinion in Application No. PCT/US2022/053653, dated Mar. 30, 2023 (45 pages).

Ding et al., "Slow-releasing rapamycin-coated bionic peripheral nerve scaffold promotes the regeneration of rat sciatic nerve after injury", Life Sciences, vol. 122 (2014), pp. 92-99.

International Search Report and Written Opinion in Application No. PCT/US2022/053642, dated Mar. 31, 2023 (14 pages).

Zheng et al., "Nanofibrous nerve guidance conduits decorated with decellularized matrix hydrogel facilitate peripheral nerve injury repair", Theranostics 2021, vol. 11, Issue 6, pp. 2917-2931.

Du et al., "Multifunctional Micro/Nanoscale Fibers Based on Microfluidic Spinning Technology", Advanced Materials 2019, vol. 31, Issue 52.

Goonoo et al., "Polydioxanone-based bio-materials for tissue engineering and drug/gene delivery applications", European Journal of Pharmaceutics and Biopharmaceutics, vol. 97, Nov. 2015, pp. 371-391.

Tajdaran et al., "Matrices, scaffolds, and carriers for protein and molecule delivery in peripheral nerve regeneration", Experimental Neurology 319 (2019) 112817.

Tajdaran et al., "A Novel Polymeric Drug Delivery System for Localized and Sustained Release of Tacrolimus (FK506)", Biotechnology and Bioengineering, vol. 112, No. 9, Sep. 2015, pp. 1948-1953.

Tajdaran et al., "Local FK506 dose-dependent study using a novel three-dimensional organotypic assay", Biotechnology and Bioengineering, vol. 116, No. 2, Feb. 2019, pp. 405-414.

Tajdaran et al., "Local delivery of FK506 to injured peripheral nerve enhances axon regeneration after surgical nerve repair in rats", Acta Biomaterialia, 96 (2019) 211-221.

* cited by examiner

DRUG DELIVERY SYSTEM AND METHODS OF USING THE SAME

CROSS-REFERENCE TO RELATED APPLICATIONS

This patent application claims the benefit of priority to U.S. Provisional Patent Application No. 63/265,861, filed on Dec. 22, 2021, the entirety of which is incorporated herein by reference.

TECHNICAL FIELD

The present disclosure relates generally to the fields of tissue repair and medicine. More particularly, the present disclosure relates to biomaterials and drug delivery platforms containing regenerative compounds, including neuro-regenerative compounds, as well as methods of making biomaterials and drug delivery platforms, and methods of treatment using these biomaterials and drug delivery platforms.

BACKGROUND

Nerve damage, regardless of cause, may result in significant, and in some cases severe, disability and dysfunction for a subject. Neuropathic injury, in particular, can cause chronic pain, loss of sensation, loss of some or all muscle control, or other undesirable effects. Addressing the deleterious effects of peripheral nerve injury is a considerable challenge, particularly when there is a delay in nerve repair or when axons are required to reestablish connections with peripheral targets over large nerve defects or long distances. In such cases, the regenerating axons often do not have the required chemical and physiological cues to effectively regenerate and reinnervate their end-target organs. For example, relatively long nerve gaps may experience a depletion of neurotrophic factors at the proximal nerve stump, and the concentration of neurotrophic factors may decline in a growth-supportive environment in the distal nerve stump.

Despite recent development in surgical techniques a limited number of patients with peripheral nerve injury recover full function. Therefore, it is desirable to develop clinically applicable techniques for treating nerve injuries and restoring sensory and functional outcomes after nerve injuries. To promote effective restoration of function and sensation following nerve injury and repair, the intervention or the treatment should support axonal regeneration and/or increase the number of neurons regenerating their axons.

SUMMARY

In accordance with the present disclosure, a biomaterial may include regenerative agent, such as a neuro-regenerative agent, or an immunosuppressive agent. The biomaterial may be useful at the site of tissue injury and direct repair (e.g., direct nerve repair) or together with an implant (e.g., a nerve graft), may be attached to an implant (e.g., secured to a surface of an implant), or may be incorporated as part of an implant. In particular, a biomaterial may include rapamycin incorporated into one or more regions or surfaces of the biomaterial that is suitable for implantation at or near an injured nerve. In this way, the biomaterial may be used to form a local drug delivery system for promoting the repair of injured tissue, for example, nerve tissue.

In one aspect, a method of preparing an implantable biomaterial may include combining a polymer with a neuroregenerative agent or immunosuppressive agent selected from a group comprising at least one of: rapamycin, cyclosporine A, or analogs thereof, melting the polymer, and extruding the polymer and the neuro-regenerative agent or immunosuppressive agent to form the implantable biomaterial.

In another aspect, a method of preparing an implantable biomaterial may include combining a polymer with rapamycin, melting the polymer, and extruding the polymer and rapamycin to form the implantable biomaterial.

In another aspect, an implant may include polydioxanone and a neuro-regenerative agent or immunosuppressive agent selected from a group comprising at least one of: rapamycin, cyclosporine A, or analogs thereof, combined with the polydioxanone.

In another aspect, an implant may include a polymer and rapamycin combined with the polymer.

Other objects, features, and advantages of the present disclosure will become apparent from the following detailed description. It should be understood, however, that the detailed description and the examples, while indicating exemplary embodiments of the present disclosure, are given by way of illustration only, since various changes and modifications within the spirit and scope of the invention will become apparent to those skilled in the art from this detailed description. Note that simply because a particular compound is ascribed to one generic formula does not mean that it cannot also belong to another generic formula.

The singular forms "a," "an," and "the" include plural reference unless the context dictates otherwise. The terms "approximately" and "about" refer to being nearly the same as a referenced number or value. As used herein, the terms "approximately" and "about" generally should be understood to encompass±10% of a specified amount or value. The use of the term "or" in the claims and specification is used to mean "and/or" unless explicitly indicated to refer to alternatives only or the alternatives are mutually exclusive, although the disclosure supports a definition that refers to only alternatives and "and/or." As used herein "another" may mean at least a second or more. As used herein, the terms "implantation" and "implant" do not require placement within a subject such that the implant is under skin or other tissue. Rather the term "implant" additionally encompasses patches for placement on skin tissue, wraps for skin tissue, and devices for placement on or near mucous membranes or on a surface of other tissue.

Embodiments of this disclosure involve the use of a neuro-regenerative or an immunosuppressive agent. As used herein, the phrase "neuro-regenerative or immunosuppressive agents" refers to: one or more neuro-regenerative agents and the absence of an immunosuppressive agent, the absence of one or more neuro-regenerative agents and the presence of an immunosuppressive agent, a single neuro-regenerative agent and a single immunosuppressive agent that are different from each other, the presence of a single agent that is both a neuro-regenerative agent and an immunosuppressive agent (e.g., rapamycin), a plurality of neuro-regenerative agents and a plurality of immunosuppressive agents, a single neuro-regenerative agent and a plurality of immunosuppressive agents, or a plurality of neuro-regenerative agents and a single immunosuppressive agent, regardless of whether the phrase "neuro-regenerative or immunosuppressive agent" is presented in singular or plural form, or shortened to the term "agent(s)" or "agent". Further, although neuro-regenerative agents for nerve repair are described herein, it is contemplated that regenerative agents suitable for use with tissues other than nerves may be used Both the foregoing general description and the following detailed description are exemplary and explanatory only and are not restrictive of the features, as claimed. As used herein, the terms "comprises," "comprising," "including," "having," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." In addition, the term "between" used in describing ranges of values is intended to include the minimum and maximum values described herein.

The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of exemplary embodiments presented herein.

DETAILED DESCRIPTION

Figure 1:
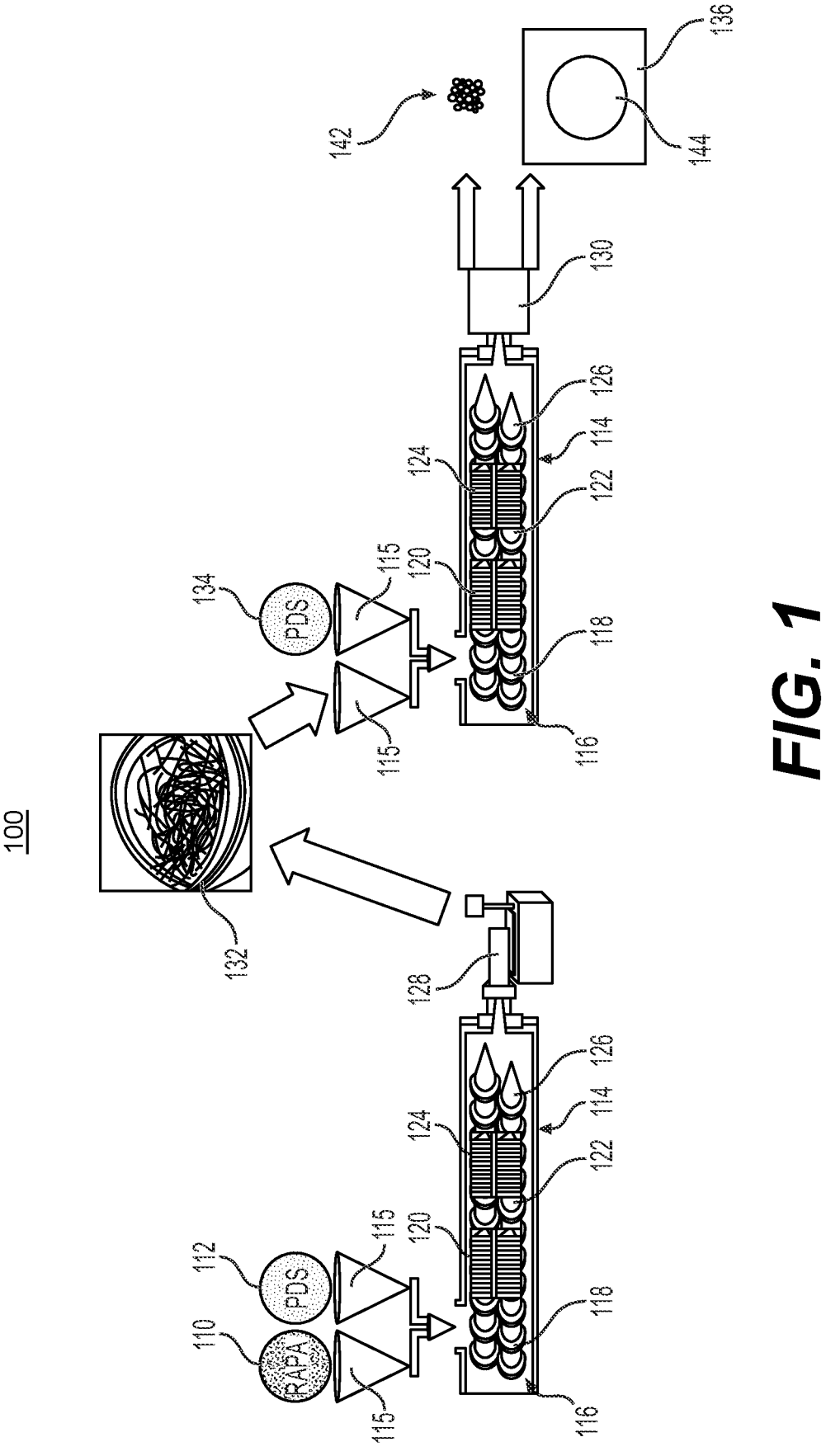
FIG. 1 shows a schematic diagram of an exemplary process for incorporating one or more neuro-regenerative or immunosuppressive agents in a polymer, according to aspects of the present disclosure.

The biomaterials that serve as a local drug delivery device and implants of the present disclosure may incorporate one or more neuro-regenerative or immunosuppressive agents in a polymeric material. The biomaterial may be attached to or included in a nerve implant (e.g., a nerve wrap, nerve connector, pre-rolled nerve wrap, nerve graft, etc.), or may be implanted separately (e.g., at or near the site of an injury or other location at which a nerve implant has been or will be implanted) to form a local drug delivery device. The biomaterial may have a suitable shape, such as one or more fibers, rods, beads, pellets, spheres, particles, sheets, films, caps, tubes, etc., of any suitable dimensions (e.g., inside diameter, outside diameter, length, width, total thickness, wall thickness, etc.). In at least some embodiments, the biomaterial may be in the form of an injectable. For example, the biomaterial may include an injectable carrier (e.g., an injectable polymer including a hydrogel, a colloidal dispersion such as a colloidal gel, and/or micelles). The injectable biomaterial may incorporate the one or more neuro-regenerative or immunosuppressive agents. The one or more regenerative, e.g., neuro-regenerative, or immuno-suppressive agents may be distributed throughout the bio-material or localized on one or more surfaces or more regions of the biomaterial. The biomaterial may be distributed throughout a tissue implant, such as a nerve implant, may be localized in one or more surfaces or regions of a tissue implant, or may form a part or the entirety of the structure of the tissue implant. The biomaterials of the present disclosure may promote tissue regeneration, e.g., nerve regeneration, which, in some aspects, may, in turn, improve nerve regeneration outcomes. Exemplary biomaterials, related methods for their preparation, and related methods of treatment using biomaterials, are described in detail below. While the local drug delivery systems, biomaterials, implants, and methods herein as discussed with respect to use at a nerve site, the local drug delivery systems, biomaterials, implants, and method may be applied to other types of tissues and other locations in a subject.

The biomaterial may include a polymer that is compatible for use in conjunction with a nerve implant. The polymer may be compatible with one or more neuro-regenerative or immunosuppressive agents. The polymer may be biodegradable following implantation in a human or non-human animal. The polymer may comprise homopolymers, copolymers, and/or polymeric blends including one or more of the following monomers: glycolide, lactide, caprolactone, dioxanone, trimethylene carbonate, monomers of cellulose derivatives, and monomers that polymerize to form polyesters. The polymer may include polydioxanone (PDS), poly-caprolactone (PCL), polytrimethylene carbonate, polygly-colide (PGL), poly-3-hydroxybutyrate (PHB), poly(3-hydroxybutyrate-co-3-hydroxyvalerate) (PHBV), poly (propylene carbonate) (PPC), poly(butylene succinate) (PBS), poly(propylene fumarate) or (PPF). The polymer may be formulated by two or more of these monomers. The polymer may be co-polymerized with lactide and/or gly-colide. The polymer may be a copolymer that includes dioxanone co-polymerized with lactide and/or glycolide such that polymerized dioxanone forms a majority of the polymer, by weight. The polymer may include polylactic acid (PLA) or poly(lactic-co-glycolic acid) (PLGA). However, in some aspects, the polymer may be free of one or both of PLA and PLGA.

The one or more neuro-regenerative or immunosuppres-sive agents may include an immunophilin ligand. The one or more neuro-regenerative or immunosuppressive agents may include rapamycin (sirolimus) and/or cyclosporine A. In a particular example, the one or more neuro-regenerative or immunosuppressive agents may include rapamycin. The one or more neuro-regenerative or immunosuppressive agents may include one or more so-called "-olimus" drugs instead of or in addition to rapamycin. For example, the one or more neuro-regenerative or immunosuppressive agents may include temsirolimus, everolimus, ridaforolimus (deforolimus), biolimus (umirolimus), novolimus, zotarolimus, myolimus, and/or amphilimus. The one or more neuro-regenerative or immunosuppressive agents may be hydrophobic, with a melting point below about 220 degrees Celsius, below about 200 degrees Celsius, or below about 190 degrees Celsius.

While agents that are neuro-regenerative and/or immunosuppressive are discussed herein, other agents may be incorporated. For example, one or more agents may be anti-inflammatory. In at least some aspects, one or more agents may prevent or inhibit growth or regeneration (e.g., regeneration of nerve tissue). For example, implants, such as a nerve wrap, may include one or more regeneration-inhibiting agents to reduce or eliminate formation of a neuroma or other undesirable or disorganized growth.

The one or more neuro-regenerative or immunosuppressive agents may be mixed with the polymer at any suitable concentration, as described below. The biomaterial may be manufactured by creating a so-called "masterbatch", also referred to herein as a "stock" batch of biomaterial, containing polymer and a relatively higher concentration of one or more neuro-regenerative or immunosuppressive agents than would ultimately be used for drug delivery within the body (e.g., 10% by weight of a neuro-regenerative or immunosuppressive agent, such as rapamycin). Alternatively, the biomaterial may be manufactured by combining a polymer with a neuro-regenerative or immunosuppressive agent without the use of a stock batch (e.g., a biomaterial formed by combining one or more neuro-regenerative or immunosuppressive agents with a polymer that is free of these agents to achieve a concentration that will ultimately be useful for local drug delivery). The stock batch may be useful to provide tailoring for specific uses for local drug delivery, such that the stock batch of material may be employed in subsequent processing to produce one or more biomaterials having one of multiple possible final forms with a suitable concentration of agent, as described below. The different biomaterials created may be used as the building blocks to create different local drug delivery systems, depending on the need.

The biomaterial may be provided in a suitable form factor whether the biomaterial is an intermediate product (e.g., when the biomaterial is part of a stock batch) or a final form (e.g., a product that is intended for inclusion in or attachment to an implant, e.g., a nerve implant, or use independent of a nerve implant). The biomaterial may be formed as one or more pellets (e.g., a stock batch of biomaterial) or one or more fibers or sheets (e.g., a biomaterial for implantation). The fibers may have an approximately constant diameter, or may have a changing diameter (e.g., a diameter that changes regularly or irregularly along the length of the fiber). The fibers may be knotted such that the fibers include one or more knots, such as one or more square knots or one or more loops. The fibers may have a spiral shape, including a number of turns. The knots, when present, may be formed in a manner that enables control over the number, spacing, size, etc., of the knots.

The biomaterial may be provided in the form of one or more sheets. The sheets may include embedded fibers and/or may be a nonwoven sheet. The biomaterial may be formed via extrusion of a polymer that is shaped into one or more sheets. If desired, the biomaterial may be in the form of one or more woven sheets that include a plurality of woven polymeric fibers. The fibers of the biomaterial may include one or more neuro-regenerative or immunosuppressive agents. A biomaterial formed as a woven or non-woven sheet may include one or more patches. The patch may include the biomaterial (e.g., polymer and one or more neuro-regenerative or immunosuppressive agents) and may be surrounded by polymer free of the neuro-regenerative or immunosuppressive agents, or the sheet surrounding the patch may include the polymer and neuro-regenerative or immunosuppressive agents while the patch includes polymer that is free of the neuro-regenerative or immunosuppressive agents. The biomaterial, when in the form of a sheet, may include one or more depots, pockets or reservoirs of the one or more neuro-regenerative or immunosuppressive agents. The pockets or depots may provide a sustained supply of the neuro-regenerative or immunosuppressive agents, e.g., for local, sustained release.

The biomaterial may be in the form of one or more rods or pellets, regularly or irregularly-shaped particles, spheres, sheets, or may have any other suitable shape. When the biomaterial is in the form of beads, rods or pellets (which may be short rods), the biomaterial may have an approximately constant diameter (e.g., a diameter that is approximately the same along the length of each rod). A plurality of rods may have approximately the same length. Alternatively, the biomaterial may include a plurality of pellets having diameters and/or lengths within a desired range, with individual pellets having differing diameters and/or lengths. The biomaterial may be formed so as to include a plurality of particles, spheres, or other shapes having similar or differing lengths and/or diameters.

In some aspects, the biomaterial may be integrated with a nerve implant (e.g., one or more portions of the implant may be formed of or may incorporate the biomaterial), the biomaterial may be attached to the implant (e.g., the biomaterial may be connected to an interior or exterior portion of the implant), or the biomaterial may be implanted at the same area as a nerve implant. The biomaterial may have any suitable form factor, whether integrated with an implant, attached to an implant, or implanted in the same area as an implant. The nerve implant may be provided for various uses, including use as a nerve connector, nerve wrap, nerve graft, nerve protector, etc. In particular, the biomaterial may be provided as part of, or for use with, implants such as those described in U.S. patent application Ser. No. 15/344,908, filed on Nov. 7, 2016, which issued as U.S. Pat. No. 10,835,253; U.S. patent application Ser. No. 15/252,917, filed on Aug. 31, 2016, which issued as U.S. Pat. No. 10,945,737; U.S. patent application Ser. No. 15/900,971, filed on Feb. 21, 2018, which issued as U.S. Pat. No. 10,813,643; U.S. Ser. No. 16/381,860, filed on Apr. 11, 2019, which issued as U.S. Pat. No. 11,166,800; U.S. patent application Ser. No. 16/192,261, filed on Nov. 15, 2018, which issued as U.S. Pat. No. 11,477,558; U.S. patent application Ser. No. 14/036,405, filed on Sep. 25, 2013, which issued as U.S. Pat. No. 9,629,997; U.S. application Ser. No. 16/898,224, filed on Jun. 10, 2020; or U.S. patent application Ser. No. 17/451,489, filed on Oct. 20, 2021.

While the implant may be a nerve implant, the implant may be an implant other than a nerve implant. Any of the biomaterials discussed herein may be useful with implants other than nerve implants. In some aspects, the biomaterials and/or implants may be useful for vascular implantation, implantation into or placement on the surface of skin (e.g., as a topical, a transdermal patch, etc.), skeletal implantation, spinal implantation, urological implantation, tendon implantation, muscular implantation, and/or others. The one or more neuro-regenerative or immunosuppressive agents may, when incorporated within an implant other than a nerve implant, be an immunosuppressive agent. These agents may
have other properties that are beneficial to the location of
implantation, and/or may be provided with additional com-
pounds that provide beneficial properties. For example, an
implant intended for vascular implantation may include an
antiproliferative agent that inhibits neointimal hyperplasia,
such as paclitaxel, in addition to one or more immunosup-
pressive agents.

When the implant is a nerve implant, the nerve implant
may be formed with tissue, e.g., nerve graft tissue. For
example, nerve tissue may be coated or impregnated with
the biomaterial. In one aspect, pellets or fibers of the
biomaterial may be coated on or impregnated into the tissue
graft. In addition or alternatively, the implant may be loaded
with one or more immunosuppressive agents in a solubilized
form, a micronized form, or powdered form for use as an
injectable implant. Nerve graft tissue suitable for processing
according to the methods herein may be natural or synthetic.
For example, the tissue may be soft biological tissue
obtained from an animal, such as a mammal, including a
human or a non-human mammal, or a non-mammal, includ-
ing a fish, amphibian, or insect. The tissue may be allogeneic
or xenogeneic to a subject into which the graft is implanted.
The tissue may be nerve tissue, including, for example,
peripheral nerve tissue or central nervous system tissue.
Other types of tissue suitable for the present disclosure
include, but are not limited to epithelial tissue, connective
tissue, muscular tissue, capillary tissue, dermal tissue, skel-
etal tissue, smooth muscle tissue, cardiac tissue, and adipose
tissue. As mentioned above, the soft biological tissue may be
mammalian tissue, including human tissue and tissue of
other primates, rodent tissue, equine tissue, canine tissue,
rabbit tissue, porcine tissue, or ovine tissue. In addition, the
tissue may be non-mammalian tissue, selected from piscine,
amphibian, or insect tissue. The tissue may be a synthetic tissue, such as, but not limited to, laboratory-grown or
3D-printed tissue. According to some examples, the tissue is
nerve tissue obtained from an animal, such as a human or a
non-human mammal. The tissue may be obtained and/or
treated as disclosed in U.S. patent application Ser. No. 17/411,718, entitled "Nerve Grafts and Methods of Prepa-
ration Thereof," filed on Aug. 25, 2021, the entirety of which
is incorporated by reference. In at least some embodiments,
an exemplary tissue may be a processed human nerve
allograft, such as an Avance® Nerve Graft from Axogen,
Inc. (Alachua, FL, US).

Although embodiments of the disclosure are described in
relation to biomaterials useful for nerve injury, and in
particular, to nerve implants for peripheral nerve injury, it is
contemplated that other types of tissue, including any of the
materials described above, may be used in the methods and
implants described herein.

FIG. 1 illustrates a diagram of an exemplary process 100
for producing a biomaterial, such as biomaterial 142 (par-
ticles such as spheres, pellets, etc., being shown in FIG. 1)
and/or biomaterial 144 (fibrous biomaterial collected on a
spool as shown in FIG. 1), which may include a polymer and
an immunosuppressive or neuro-regenerative agent. Bioma-
terials 142 and 144 may be suitable for implantation in a
human or non-human animal. For example, biomaterials 142 and 144 may be suitable for use with a nerve implant and/or
for implantation in a human or non-human animal. A bio-
material 132 may also be formed in process 100. Biomaterial
132 may form a "stock batch" of biomaterial, as described
in detail below.

Figure 2:
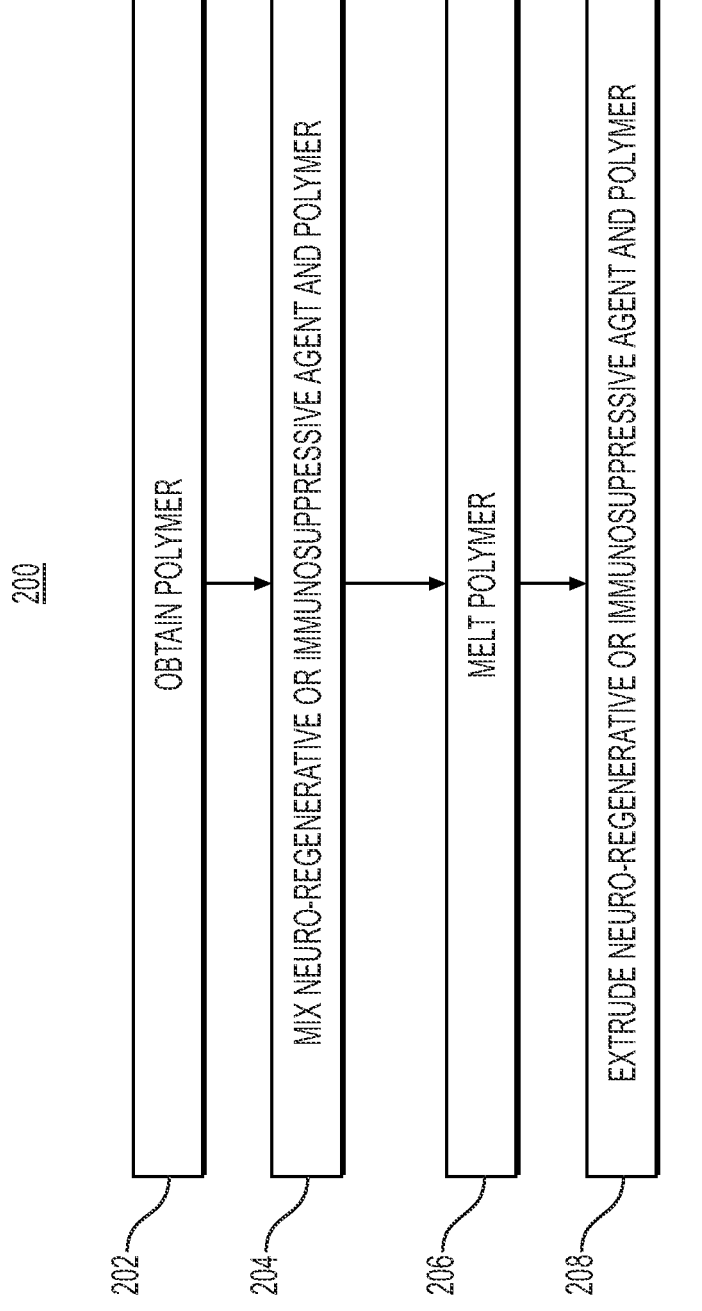
FIG. 2 shows a flowchart of an exemplary process for incorporating one or more neuro-regenerative or immuno-suppressive agents in a polymer, according to aspects of the present disclosure.

FIG. 2 illustrates a flowchart of an exemplary process 200
for producing a biomaterial that includes a polymer and one or more immunosuppressive or neuro-regenerative agents
such as rapamycin. While process 200 is described in
conjunction with process 100 and FIG. 1 below, as under-
stood, process 200 may include fewer steps, additional steps,
and/or different steps as compared to process 100. Addition-
ally, process 200 may include fewer steps, additional steps,
and/or different steps as compared to each block (e.g., steps
202, 204, 206, and 208) illustrated in FIG. 2, or the specific
order of the steps may be different.

In a step 202 (FIG. 2), a polymer 112 (FIG. 1) may be
obtained. Polymer 112 may include a polyester. Polymer 112
may include polydioxanone (PDS), polycaprolactone (PCL),
polyglycolide (PGL), poly-3-hydroxybutyrate (PHB), poly
(3-hydroxybutyrate-co-3-hydroxyvalerate) (PHBV), poly
(propylene carbonate) (PPC), poly(butylene succinate)
(PBS) and poly(propylene fumarate) (PPF). Polymer 112
may include polylactic acid (PLA) or poly(lactic-co-glycolic
acid) (PLGA). However, in at least some embodiments,
polymer 112 may be free of both PLA and PLGA. Forming
polymer 112 free of both PLA and PLGA may allow
biomaterial 142 to avoid the generation of acid at the site of
implantation that may occur when PLA or PLGA degrades
following implantation.

The obtained polymer 112 may be in any suitable form,
such as powder, filaments, particles (spheres, pellets, etc.),
among others. For example, polymer 112 may be a substan-
tially-pure powder that is suitable for mixing with the one or
more immunosuppressive or neuro-regenerative agents,
which may also be in a powdered form. If desired, step 202
may include synthesizing polymer 112. For example, when
polymer 112 is PDS, polymer 112 may be obtained by
ring-opening polymerization of p-dioxanone. When polymer
112 is in a form other than a powder, step 202 may include
forming a powder from another form of polymer 112 (e.g.,
particles, filament, etc.) by grinding particles, filaments,
pellets, or another structure of polymer 112 to obtain a
powder of polymer 112 with grains and/or particles that have
a suitable size to facilitate homogenous mixing of polymer
112 and immunosuppressive or neuro-regenerative agent
110.

In a step 204 (FIG. 2), the one or more immunosuppres-
sive or neuro-regenerative agents 110 (FIG. 1) and polymer
112 may be mixed together. The one or more immunosup-
pressive or neuro-regenerative agents 110 may include an
immunophilin ligand. The one or more immunosuppressive
or neuro-regenerative agents 110 may include a calcineurin
inhibitor. The one or more immunosuppressive or neuro-
regenerative agents 110 may include rapamycin and/or
cyclosporine A, including analogs thereof (e.g., analogs of
rapamycin, such as temsiroliumus, everolimus, ridaforoli-
mus, biolimus, novolimus, zotarolimus, myolimus, and/or
amphilimus).

In some examples, the one or more immunosuppressive or
neuro-regenerative agent(s) 110 may include rapamycin.
Agent(s) 110, such as rapamycin, may inhibit the mamma-
lian target of rapamycin (mTOR), which regulates process
that affect cell growth, cell proliferation, and/or related
cellular activities. The presence of rapamycin in a subject
may facilitate nerve regeneration. Rapamycin may interact
with immunophilins, such as FK506 binding proteins, in
axons, which in turn can activate pathways that improve
axonal regeneration. Rapamycin may also bind to mTOR
Complex 1 and inhibit mTOR activity. By inhibiting mTOR
activity, rapamycin may reduce mTOR-mediated immune
response in the presence of an implant, such as an allograft.

The one or more immunosuppressive or neuro-regenera-
tive agent(s) 110 may be employed in biomaterials intended for use in a subject that experienced a nerve injury. When used in these biomaterials, agents 110 may facilitate healing and/or regeneration of nerve tissue of this subject and may cause immunosuppression. When the one or more immunosuppressive or neuro-regenerative agents 110 includes an immunophilin ligand, agent(s) 110 may include rapamycin, either alone or in combination with another immunophilin ligand, e.g., cyclosporine A.

Mixing may include physically blending agent(s) 110 and polymer 112. For example, agent(s) 110 and polymer 112, one or both of which are present in powdered form, may be thoroughly mixed together to produce uniform, homogenously-mixed blend of pellets having a desired ratio of agent(s) 110 to polymer 112. While agent(s) 110 and polymer 112 may be mixed when both are in a solid state, one or both of agent(s) 110 and polymer 112 may be in a liquid form during mixing. For example, agent(s) 110 and polymer 112 may be heated, dissolved in a solvent, etc., to create a liquid form suitable for mixing with another liquid. In embodiments where agent(s) 110 and polymer 112 are mixed while in a liquid form, melting agent(s) 110 and polymer 112 in step 206, described below, may be omitted.

Agent(s) 110 and polymer 112 may be provided separately to a single system or single device that is configured to both mix agent(s) 110 and polymer 112, and to melt polymer 112 (as described below with respect to step 206 of method 200). For example, as shown in FIG. 1, an extruder 114 may include a plurality of feeding devices, such as hoppers, for separately receiving agent(s) 110 and polymer 112 in a solid form (e.g., as powders). In some aspects, agent(s) 110 and polymer 112 may be mixed before polymer 112 is supplied to a device for melting polymer 112 (described below with respect to step 206 of method 200). In these examples, one or more devices may facilitate the performance of step 204 in which agent(s) 110 and polymer 112 are mixed, while one or more additional devices may facilitate the performance of step 206 in which the polymer 112 is melted (e.g., by supplying a homogenous mix of agent(s) and polymer 112).

In examples where the one or more immunosuppressive or neuro-regenerative agents 110 and polymer 112 are supplied to separate feeders for extruder 114, extruder 114 may be configured to supply metered quantities of agent(s) 110 and metered quantities of polymer 112 to a mixing section 118. This may be performed with a feeder device, such as a material hopper 115 (two hoppers 115 being illustrated in FIG. 1). Hoppers 115 may be configured to feed agent(s) 110 and polymer 112 in a controlled manner in which agent(s) 110 and polymer 112 are drawn to the interior of extruder 114. Hopper 115, or other feeding device, may be configured to compensate for changes in that the agent(s) 110 and polymer 112 supplied to extruder 114, such as reductions in weight as material is depleted, in the example of gravity-fed feeding devices.

Whether agent(s) 110 and polymer 112 are mixed before being supplied to extruder 114 or are mixed by extruder 114 itself, agent(s) 110 and polymer 112 may be metered such that the ratio of agent(s) 110 to polymer 112 is precisely controlled. For example, a concentration of agent 110 may be within a range of about 0.01% by weight to about 30% by weight of the biomaterial, within a range of about 0.05% by weight to about 20% by weight, or within a range of about 0.1% by weight to about 10% by weight. In particular, the concentration of agent 110 may be about 0.1% by weight, about 1% by weight, about 2% by weight, about 3% by weight, about 4% by weight, or about 20% by weight. The concentration of agent(s) 110 in the biomaterial 132, 142, and/or 144 (described below) output from extruder 114 may be substantially the same as the concentration of agent(s) 110 received by extruder 114, or the same as the concentration of agent(s) 110 at any point within extruder 114. Regardless, the concentration of agent(s) 110 within the extruded product may be any of the above-described concentrations.

A step 206 (FIG. 2) of process 200 may include melting the polymer 112 (FIG. 1) received with extruder 114. This may include supplying the agent 110 and polymer 112 to a hopper or other input of extruder 114. Extruder 114 may be a single-screw or twin-screw extruder that includes an extruder screw 116, screw 116 having a conveying section 118, a kneading section 120, a conveying section 122, a shearing section 124, and a metering section 126. Extruder 114 may be a twin-screw extruder that includes a pair of co-rotating or counter-rotating screws 116. Screw 116 may be sized appropriately for producing biomaterial 132. For example, screw 116 may have an outer diameter within a range of about 9 mm to about 36 mm, the outer diameter being a maximum diameter of screw 116. In particular, screw 116 may have a maximum outer diameter of about 18 mm.

Conveying section 118 of extruder screw 116 may include threading sized to receive agent(s) 110 and polymer 112 and convey both materials downstream. Additionally, conveying section 118 may include a zone that includes threading having a reduced thread pitch (threading that is spaced closer together) to generate heat to begin softening polymer 112. Kneading section 120 may receive the agent 110 and polymer 112. Threads of kneading section 120 may have a geometry suitable for generating heat, by friction, to melt polymer 112. The heat generated with kneading section 120 during step 206 may be sufficient to soften and at least partially melt polymer 112 without adversely impacting the effectiveness of agent(s) 110 due to overheating. This temperature may be within a range of about 80 degrees Celsius to about 200 degrees Celsius, for example. The temperature generated with extruder 114 may be selected based on the softening and/or melting temperatures of agent 110 and polymer 112, or to avoid a temperature at which agent(s) 110 may be damaged or deactivated, e.g., denatured.

A second conveying section 122 may receive heated material from kneading section 120 and supply this material to a shearing section 124 which includes shearing or kneading threads configured to further increase the temperature of agent 110 and polymer 112. The temperature generated with shearing section 124 may be a maximum temperature generated with extruder 114. This maximum temperature within extruder 114 may be higher than a melting temperature of agent(s) 110 and higher than a melting temperature of polymer 112. In examples where agent(s) 110 is rapamycin and polymer 112 is PDS, shearing section 124 may be configured to generate a temperature within a range of about 100 degrees Celsius to about 250 degrees Celsius. For example, shearing section 124 may raise the temperature of agent(s) 110 and polymer 112 to a temperature in a range of about 150 degrees Celsius to about 250 degrees Celsius. In particular, shearing section 124 may raise the temperature of agent 110 and polymer 112 to a temperature in a range of about 175 degrees Celsius to about 225 degrees Celsius. Shearing section 124 may raise the temperature of agent(s) 110 and polymer 112 to a temperature above about 185 degrees Celsius. This temperature may be sufficient to ensure polymer 112 is in a liquid state before agent(s) 110 and polymer 112 are received by a die at a downstream end of extruder 114.

While the heat generated by extruder 114 may be generated entirely by friction caused by the rotation of extruder screw(s) 116, one or more heaters may be secured to extruder 114 to assist in the generation of a desired amount of heat and maintenance of a desired temperature at one or more locations within extruder 114. These heaters may be placed along one or more positions of the barrel of extruder 114, and may partially or entirely surround kneading section 120, shearing section 124, and/or any other sections of extruder 114. A temperature may be monitored at one or more locations along the length of extruder 114. For example, one or more temperature sensors may be positioned to detect a temperature within extruder 114. A control system, in communication with these temperature sensors, may control the heaters on the barrel of extruder 114 to maintain a desired temperature.

A step 208 (FIG. 2) may include extruding agent(s) 110 (FIG. 1) and polymer 112 with extruder 114, for example. Melted and mixed agent(s) 110 and polymer 112 may be conveyed and metered via metering section 126 downstream of shearing section 124. Metering section 126 may supply homogenized agent 110 and polymer 112 to an extruder die having an opening with a diameter of about 0.5 mm to about 2 mm, or other diameters suitable for extruding fiber having a final diameter of about 50 μm to about 200 μm (e.g., with use of a puller to draw down the diameter of the fiber). In other aspects, the extruder die may have an opening with a diameter of about 50 μm to about 200 μm for producing extruded fibers having a final diameter of about 50 μm to about 200 μm. In particular, the extruder die may have an opening with about a 1 mm diameter. The extruded material, which includes agent(s) 110 and polymer 112, may be received by a pelletizer or other shaping device 128. While metering section 126 may be formed by a downstream portion of extruder screw(s) 116, metering section 126 may include a metering pump (e.g., a gear pump) configured to push a precisely-metered quantity of combined agent(s) 110 and polymer 112, to an output of extruder 114.

Metering section 126 may supply combined agent(s) 110 and polymer 112, at a desired rate, to shaping device 128. Shaping device 128 may be any suitable device or plurality of devices configured to modify or otherwise control the shape of the product extruded with extruder 114, allowing the production of biomaterial 132 in a desired morphology. In particular, shaping device 128 may include, instead of or in addition to a pelletizer, a sheet extrusion system, a spinning system (e.g., for producing fibers), a device for forming particles, spheres, etc.

When shaping device 128 is a pelletizer (e.g., as shown in FIG. 1) shaping device 128 may be configured to cut extruded material into a plurality of pellets or rods, or other shapes, to form a biomaterial 132. Biomaterial 132 may include agent 110 and polymer 112 that are homogenously mixed and that have solidified following extrusion through extruder 114. The content of agent(s) 110 in biomaterial 132 may substantially correspond to the ratio of agent 110 to polymer 112 introduced during step 204, and may be equivalent to any of the above-described concentrations or ranges of concentration. For example, a concentration of agent 110 may be within a range of about 0.01% by weight to about 30% by weight, within a range of about 0.05% by weight to about 20% by weight, or within a range of about 0.1% by weight to about 10% by weight. In particular, the concentration of agent 110 may be about 0.1% by weight, about 1% by weight, about 2% by weight, about 3% by weight, about 4% by weight, or about 20% by weight.

In at least some embodiments, biomaterial 132 may be formed with a relatively high concentration of agent 110 so as to form a stock batch of one or more immunosuppressive or neuro-regenerative agents integrated with polymer 112. The concentration of agent 110 in a stock batch of biomaterial 132 may be within a range of about 1% by weight to about 30% by weight, or about 8% by weight to about 20% by weight. In particular, the concentration of agent 110 in a stock batch of biomaterial 132 may be about 5% by weight, about 8% by weight, about 10% by weight, about 15% by weight, or about 20% by weight.

In embodiments where biomaterial 132 is not a stock batch, biomaterial 132 may be formed with a concentration of agent 110 suitable for use with a local drug delivery device, e.g., an implant. For example, a concentration of agent 110 within biomaterial 132 may be within a range of about 0.01% by weight to about 8% by weight, within a range of about 0.1% by weight to about 6% by weight, or within a range of about 1% by weight to about 4% by weight. In particular, a concentration of agent 110 within biomaterial 132 may be about 1% by weight, about 2% by weight, about 3% by weight, or about 4% by weight.

In examples where biomaterial 132 is created as a so-called "stock" batch that is not intended for implantation without further processing, the above-described process 200 may be repeated, for example by processing biomaterial 132 with the same or a different extruder 114, or one or more other devices. An example of this further biomaterial preparation is described below with reference to a further (e.g., second or subsequent) performance of method 200 (FIG. 2) with biomaterial 132. This further performance of method 200 may facilitate the controlled reduction of the concentration of agent 110 within biomaterial 132. If desired, the further performance of method 200, described below, may facilitate the incorporation of one or more second polymers 134 that are different from polymer 112 used to produce biomaterial 132.

As an alternative to a further performance of method 200, biomaterials 132 formed as a stock batch of material may be useful for producing an implant including an injectable polymer. For example, the stock batch may be processed to create a hydrogel, a colloidal gel, and/or to form a polymer that includes micelles. The injectable implant formed by this processing may include a desired concentration of agent 110 and may be implanted in a subject at a desired site (e.g., the region of a peripheral nerve injury) by injection.

When performing method 200 with biomaterial 132, as shown in the right portion of FIG. 1, step 202 (FIG. 2) may be repeated by obtaining an additional polymer 134. This additional polymer 134 may be obtained as described above with respect to polymer 112. Additional polymer 134 may be the same polymer as polymer 112 (PDS in the example shown in FIG. 1), or polymer 134 may be different than polymer 112. When additional polymer 134 is different than polymer 112, polymer 134 may be selected so as to be compatible with polymer 134. In a particular embodiment, polymer 134 is entirely free of agent 110 and thus may be considered a "pure" polymer. Polymer 134 may be used to reduce the concentration of agent 110 in the product created by repeating method 200, as described below.

Step 204 may be repeated by mixing biomaterial 132 with additional polymer 134. For example, rods or pellets of biomaterial 132 may be mixed with pellets, spheres, powder, or another form of polymer 134. In some aspects, biomaterial 132 may be structurally modified (e.g., ground into powdered form, melted, etc.) before biomaterial 132 and polymer 134 are mixed together. Moreover, while a feeder in the form of a pair of hoppers are shown in FIG. 1, biomaterial 132 and polymer 134 may be mixed together outside of extruder 114 and introduced to extruder 114 together, in a similar manner as described above with respect to agent(s) 110 and polymer 112.

The ratio of biomaterial 132 to polymer 134 following mixing may be selected based on the desired concentration of agent 110 in a final product (e.g., biomaterial 142 or 144, which are described below) formed with the mixed biomaterial 132 and polymer 134. For example, step 204 may include mixing biomaterial 132 and polymer 134 in a 1:5 ratio to dilute a biomaterial 132 having a 10% by weight concentration of agent 110 to a final product (biomaterial 142 or 144) having a concentration of about 1% of agent 110 by weight, about 2% of agent 110 by weight, about 3% of agent 110 by weight, or about 4% of agent 110 by weight. As described above with respect to an earlier performance of step 204, biomaterial 132 and polymer 134 may be mixed prior to being introduced to a feeding device for extruder 114 or may be mixed by use of feeding devices that control the mixing of biomaterial 132 and polymer 134.

Step 206 may be repeated by introducing the mixed biomaterial 132 and polymer 134 into an extruder 114. As noted above, step 206 may be performed with the same extruder 114 as described above, or with a different extruder. The extruder used for mixing biomaterial 132 and polymer 134 may include a pair of screws 116 having the same features and sections as described above (e.g., sections 118, 120, 122, 124, and 126). Alternatively, this extruder may have different sections and/or a different number of sections. During step 206, extruder 114 may melt and homogenize biomaterial 132 and polymer 134.

Step 208 may be repeated by extruding the melted and mixed biomaterial 132 and polymer 134 through an extruder die. The extruder die may have an opening with a diameter of about 0.5 mm to about 2.00 mm. In particular, the extruder die may have an opening with about a 1.00 mm diameter. The extruder die may have other diameters suitable for extruding fiber having a final diameter of about 50 μm to about 200 μm or may have an opening with a diameter of about 50 μm to about 200 μm for producing extruded fibers having a final diameter of about 50 μm to about 200 μm. Extrusion of this mixed material may be facilitated with a shaping device 130 configured to modify the shape of the extruded material. In particular, shaping device 130 may include a puller that enables control over the diameter of extruded material by stretching the extrudate under tension to draw down the diameter. For example, the mixed biomaterial 132 and polymer 134, when in the form of a fibrous biomaterial 144, may have a diameter within a range of about 50 μm to about 600 μm, of about 100 μm to about 400 μm, or within a range of about 150 μm to about 300 μm. In particular, the material drawn with shaping device 130 (e.g., a puller) may have a diameter of about 150 μm, about 200 μm, about 250 μm, or about 300 μm. When forming a biomaterial having a fibrous morphology, shaping device 130 may be used in conjunction with a winding device or winder 136. Winder 136 may be configured to collect the extruded and suitably-shaped fibrous biomaterial 144.

Step 208 may further include one or more processing steps to produce a biomaterial in a desired form or shape, such as biomaterial 142 formed in the shape of short rods or pellets (pellets being shown for biomaterial 142), or biomaterial 144 formed in the shape of one or more fibers collected on a winder 136. While particular examples are described below, step 208 may include forming a biomaterial that includes agent 110 and polymer 112 as fibers (including knots, free of knots, in spiral form, straight, including one or more bends, etc.), a sheet, rods, pellets, cylinders, particles, spheres, or another shape. Agent(s) 110 may be incorporated within polymer 112 without the need to encapsulate agent(s) 110 such that a core of agent(s) are surrounded by a shell of polymer. Encapsulation may be avoided, for example, through homogenous integration of agent(s) 110 and polymer 112. Agent(s) 110 may be incorporated within polymer 112 in a crystalline form. This crystalline form of agent(s) 110 may be present in a biomaterial having any of the shapes described herein (e.g., a fiber, sheet, rod, pellet, cylinder, particles, spheres, etc.). However, if desired, agent(s) 110 may be provided entirely in an amorphous form, or as a mixture of amorphous and crystalline forms.

Step 208 may result in a biomaterial 142 or 144 that includes a uniformly distributed agent 110. In examples where agent 110 includes rapamycin, the biomaterial 142 or 144 may be formed free of FK506. Additionally, each biomaterial described herein, includes biomaterials 132, 142, and 144, described above, and/or biomaterials 302, 352, 402, 422, 442, and 462, described below, may include rapamycin while being free of FK506. Further, implant 400, 420, 440, and 460, described below, may include rapamycin while being free of FK506. In some aspects, it may be beneficial to form a biomaterial and/or an implant with rapamycin and without FK506. The use of rapamycin as agent 110, either alone or with another agent 110 other than FK506, may introduce advantages as compared to implants that include FK506. In at least some examples, rapamycin, when included in a biomaterial and/or implant as described herein, may provide neuroregenerative benefits, including an increased rate of nerve regeneration, an increased number of neurons that are able to regenerate their axons, and others. Additionally, rapamycin may provide benefits such as lower nephro-toxicity, reduced risk of causing or contributing to hypertension, and less neoplastic potential, in a subject, as compared to FK506. Rapamycin may also provide for improved stability when incorporating an agent 110, including rapamycin, in a polymer 112, during the process for forming biomaterials 132, 142, 144, 302, 352, 402, 422, 442, and/or 462. This improved stability may be due to the higher melting temperature of rapamycin as compared to that of FK506, and/or other characteristics of rapamycin. One or more of these benefits may be realized and/or increased by employing the biomaterials or implants described herein in a localized manner, e.g., at the site of a peripheral nerve injury.

Figure 3B:
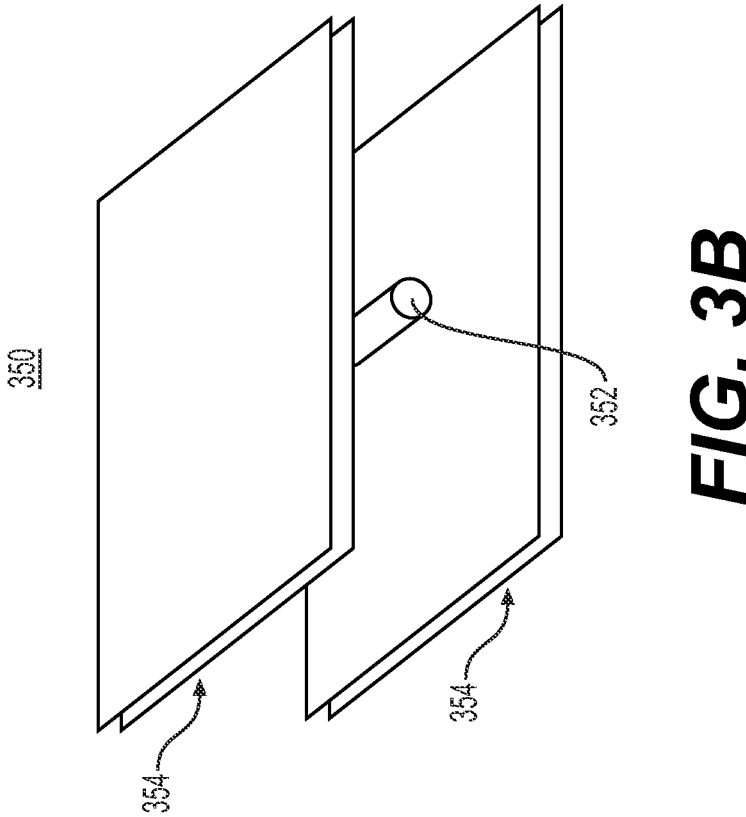
FIG. 3B shows an exemplary biomaterial including one or more neuro-regenerative or immunosuppressive agents, according to aspects of the present disclosure.
Figure 3A:
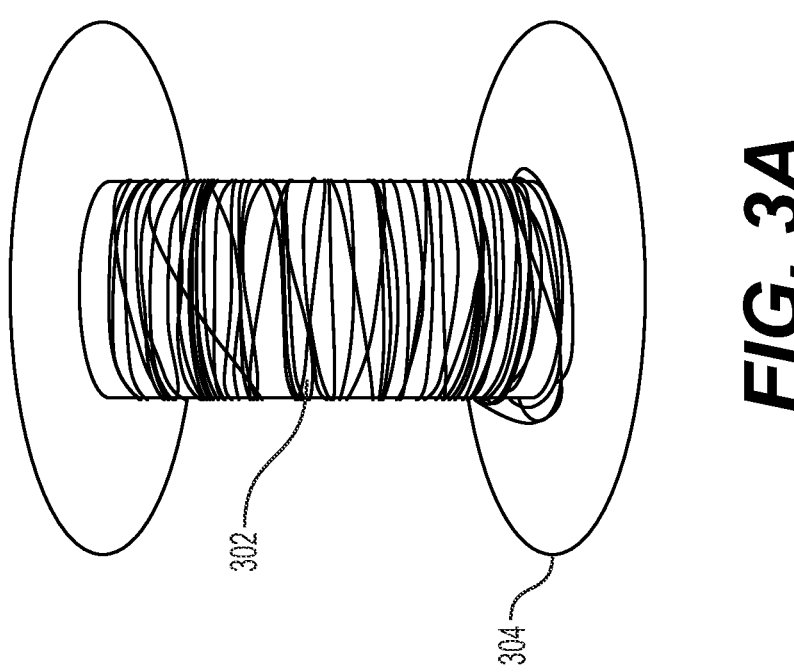
FIG. 3A shows an exemplary biomaterial including one or more neuro-regenerative or immunosuppressive agents, according to aspects of the present disclosure.

FIG. 3A illustrates an exemplary biomaterial 302 in the form of fibers that may be produced by fiber extrusion, for example, in which biomaterial 302 is collected on a spool 304 (e.g., by winder 136). Fibers of biomaterial 302 may have a desired diameter (e.g., a diameter established by extruder 114 and/or shaping device 130, such as a diameter within a range of about 50 μm to about 3 mm, a range of about 100 μm to about 2.5 mm, or a range of about 250 μm to about 2 mm. In some aspects, shaping device 130 may reduce the diameter of fibers of biomaterial 302 such that these fibers have a final diameter within a range of about 50 μm to about 600 μm, of about 100 μm to about 400 μm, or within a range of about 150 μm to about 300 μm). A concentration of agent(s) 110 in these fibers may be within a range of about 0.01% by weight to about 30% by weight, within a range of about 0.05% by weight to about 20% by weight, or within a range of about 0.1% by weight to about 10% by weight. In particular, the concentration of agent 110 may be about 0.1% by weight, about 1% by weight, about 2% by weight, about 3% by weight, about 4% by weight, about 10% by weight, or about 20% by weight.

FIG. 3B illustrates an exemplary biomaterial assembly 350, which may be formed from biomaterial 144 or 302, for example. Biomaterial assembly 350 may be formed with one or more fibers 352 secured within one or more layers 354 of bio-compatible material, such as a natural material. The material of layers 354 may include, for example, porcine small intestine submucosa ("SIS"), amnion-based tissue (e.g., amniotic/chorionic membrane), or reconstituted denatured collagen. If desired, layers 354 may include one or more synthetic materials instead of or in addition to a natural material, such as SIS. Suitable synthetic materials for use as layers 354 or inclusion in layers 354 may include a reabsorbable polymer formed as one or more layers in a non-woven or woven structure, include homopolymers, copolymers, and/or polymeric blends of one or more of the following monomers: glycolide, lactide, caprolactone, dioxanone, or trimethylene carbonate, monomers of cellulose derivatives, or monomers that polymerize to form polyesters. Additional synthetic materials that may be included in layers 354 instead of, or in addition to a natural material, include silicone membranes, expanded polytetrafluoroethylene (ePTFE), polyethylene tetraphthlate (Dacron), polyurethane aliphatic polyesters, poly(amino acids), poly(propylene fumarate), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and blends thereof. Natural polymers suitable for use as material layers 354 or inclusion in material layers 354 may include collagen, elastin, thrombin, fibronectin, starches, poly(amino acid), gelatin, alginate, pectin, fibrin, oxidized cellulose, chitin, chitosan, tropoelastin, hyaluronic acid, fibrin-based materials, collagen-based materials, hyaluronic acid-based materials, glycoprotein-based materials, cellulose-based materials, silks and combinations thereof.

Biomaterial 352 and layers 354 of biomaterial assembly 350 may be formed in one of various form factors. For example, biomaterial 352 may be in the form of a fiber with a suitable diameter and length. While FIG. 3B illustrates a single fibrous biomaterial sandwiched between a plurality of material layers 354, a plurality of biomaterials 352 (e.g., a plurality of individual fibers, pellets, spheres, springs, etc.) having the same shape or different shapes may be provided between one or more material layers 354.

Biomaterial 302 and/or biomaterial 352 of biomaterial assembly 350 may have been formed by using one or more of biomaterials 132, 142, and 144. For example, biomaterial 132 may be produced as a stock batch for use in a universal localized delivery system. The localized delivery system may be formed by diluting biomaterial 132 (e.g., by mixing biomaterial 132 and polymer 134 as described above) and forming biomaterial 142 and/or 144, or a biomaterial having any other suitable form factor. Thus, these biomaterials may enable a modular localized drug delivery system useful with implants 400, 420, 440, and/or 460 described below.

Exemplary form factors and uses of biomaterials 352 are described below with respect to implants 400, 420, 440, and 460, as shown in FIGS. 4A-4D. While FIGS. 4A-4D illustrate fiber-shaped biomaterials 402, 422, 442, and 462, as understood, each of the biomaterials in FIGS. 4A-4D may have any of the above-described shapes or may be provided as a plurality of biomaterials in any combination of these shapes. Biomaterials 402, 422, 442, and 462 may be attached to implants 400, 420, 440, and 460 by wrapping one or more sheets of material, such as layers 354, around the structure of the corresponding implant, which may have a cylindrical or generally tubular shape, to attach the biomaterials 402, 422, 442, 462 to the implant. Alternatively, layers 354 may form the structure of the corresponding implant, such as implants 400, 420, and 440. For example, implants 400, 420, and 440 may include SIS material, as described above with respect to biomaterial assembly 350, this SIS material forming the body of the implant. As understood, any of the materials described above with respect to material layers 354 may be employed instead of or in addition to SIS material. Implant 460 (FIG. 4D) is an example of an implant formed of nerve graft material, such as decellularized tissue from a human or non-human source, other natural material, and/or synthetic material.

Figures 4A, 4B, 4C, 4D:
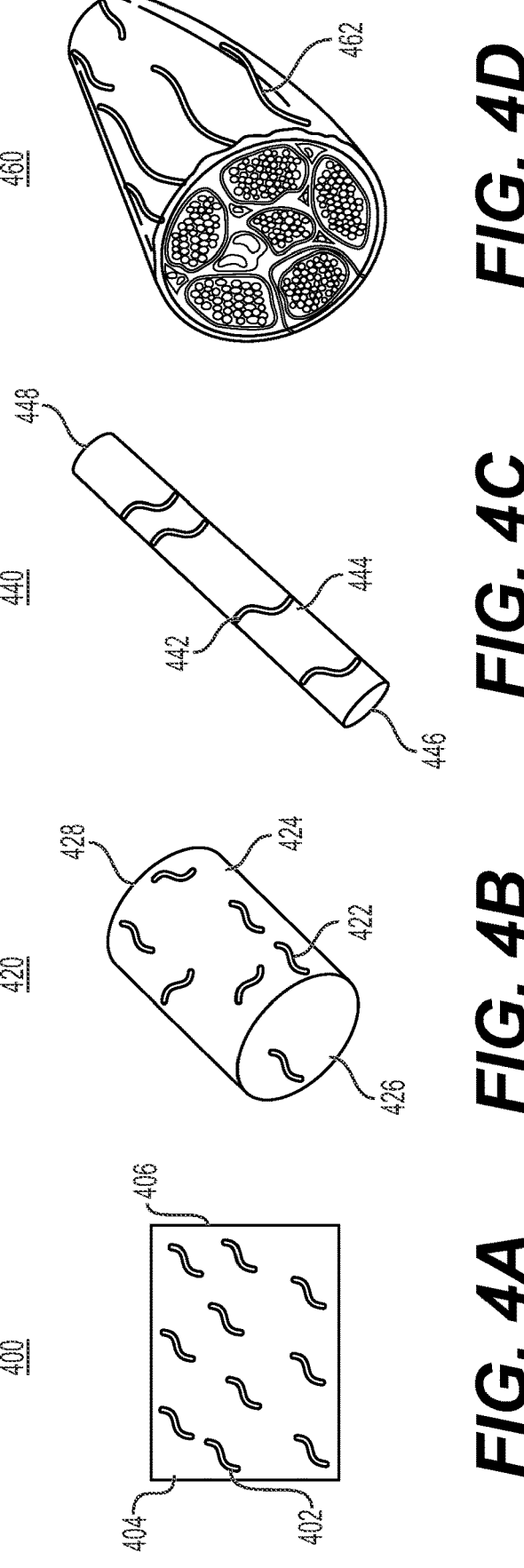
FIG. 4A shows an exemplary nerve wrap implant including a biomaterial with one or more neuro-regenerative or immunosuppressive agents, according to aspects of the present disclosure.
FIG. 4B shows an exemplary nerve connector implant including a biomaterial with one or more neuro-regenerative or immunosuppressive agents, according to aspects of the present disclosure.
FIG. 4C shows an exemplary pre-rolled nerve wrap implant including a biomaterial with one or more neuro-regenerative or immunosuppressive agents, according to aspects of the present disclosure.
FIG. 4D shows an implant including a biomaterial with one or more neuro-regenerative or immunosuppressive agents, according to aspects of the present disclosure.

FIG. 4A illustrates an exemplary implant 400 that may be suitable for implantation in a subject. In some aspects, implant 400 may be useful as a nerve wrap that is configured to be implanted at the site of a peripheral nerve injury in a subject. Implant 400 may be formed by attaching or embedding one or more biomaterials 402, such as fibers, at one or more locations of implant 400. For example, one or more biomaterials 402 may be attached to and/or embedded throughout implant 400. Implant 400 may be in the form of a substantially rectangular sheet (as shown in FIG. 4A), a circular sheet, or a sheet having other regular or irregular shapes. While one sheet is shown in FIG. 4A, implant 400 may include a plurality of sheets stacked and secured together. Proximal and distal ends 404 and 406 of implant 400 may be suitable for being secured (e.g., with sutures) to soft tissue so as to form a barrier that protects nerve tissue during healing.

In some aspects, implant 400 may be rectangular, having a length measured from proximal end 404 to distal end 406 that is longer than a width of implant 400 measured in a direction perpendicular to the length. In particular, implant 440 may have a length, as measured from proximal end 404 to distal end 406, within a range of about 5 mm to about 60 mm, within a range of about 10 mm to about 50 mm, or within a range of about 20 mm to about 40 mm. In particular, cylindrical body 444 may have a length of about 20 mm or about 40 mm.

Biomaterials 402 of implant 400 may be provided at different locations throughout implant 400. In some aspects, a higher concentration of biomaterials 402 may be provided at a location of implant 400 that is expected to be positioned adjacent to an injured nerve, such as a end. In such cases, a higher concentration of agent(s) 110, such as rapamycin, may be provided at proximal end 404, at distal end 406, and/or at an axial center portion including the halfway-point between ends 404 and 406. This may be achieved by placing a higher concentration of biomaterials 402 at proximal end 404, distal end 406, and/or the axial center portion of implant 400. Alternatively, biomaterials 402 may be substantially consistently and regularly distributed throughout the entirety of implant 400. In some aspects, biomaterials 402 may include fibers that are oriented in a desired manner. For example, as shown in FIG. 4A, these fibers may extend so as to be generally parallel to each other. Other distributions, as described below with respect to implants 420, 440, and 460, may also be employed in implant 400. Additionally, while biomaterials 402 may include a neuro-regenerative or immunosuppressive agent, biomaterials 402 of implant 400 may include one or more growth-inhibiting agents that, e.g., may prevent or reduce the formation of a neuroma.

FIG. 4B illustrates an exemplary implant 420 that may be suitable for implantation in a subject. In some aspects, implant 420 may be useful as a nerve connector that is configured to be implanted at the site of a peripheral nerve injury in a subject. Implant 420 may include a cylindrical body 424 defining a proximal end 428 and a distal end 426 that are configured for attachment (e.g., via sutures) to a proximal nerve end and a distal nerve end, respectively. In some aspects, tubular body 424 may define a diameter within a range of about 0.5 mm to about 10 mm, about 1.0 mm to about 8 mm, or about 1.5 mm to about 7 mm. In particular, a diameter of cylindrical body 424 may be equal to about 1.5 mm, about 2.0 mm, about 3.0 mm, about 4.0 mm, about 5.0 mm, about 6.0 mm, or about 7.0 mm. A length of cylindrical body 424 of implant 420 may be within a range of about 5 mm to about 20 mm, or within a range of 10 mm to about 15 mm. In particular, a length of cylindrical body 424 may be equal to about 10 mm or equal about 15 mm.

As shown in FIG. 4B, biomaterials 422 of implants 420 may be in fibrous form, with fibers extending in different orientations. Alternatively, implant 420 may include fibrous biomaterials 422 that are generally aligned or parallel, or distributed in one or more of the manners described herein with respect to implants 400, 440, and/or 460. While the distribution of biomaterials 422 may be generally uniform, if desired, a higher concentration of biomaterials 422, and thus, a higher concentration of rapamycin, may be present at proximal and distal ends 428 and 426 of implant 420, or at a central region of implant 420. This may provide a localized concentration of rapamycin at the proximal and distal nerve ends of a subject. Although implant 420 is shown as a tube, in some aspects, implant 420 may start as a flat sheet, e.g., a rectangular sheet, and then may be wrapped around one or more nerves during implantation to form a tube.

FIG. 4C illustrates an exemplary implant 440 that may be suitable for implantation in a subject. In some aspects, implant 440 may extend from a proximal end 448 to distal end 446 to define a rod or cylinder with a hollow interior (like implant and 420) that may be useful as a nerve protector. Implant 440 may be a pre-rolled version of implant 400. Implant 440 may be configured to be implanted at the site of a peripheral nerve injury in a subject. In particular, implant 440 may be configured for attachment at a peripheral nerve injury site to provide a structural barrier for protecting one or more peripheral nerves or nerve ends, as well as structural reinforcement to support peripheral nerve reconstruction and healing. Implant 440 may include a cylindrical body 444 formed in the shape of a rod or tube. In some aspects, implant 440 may have a length that is longer than a length of implant 420. In particular, cylindrical body 444 of implant 440 may have a length, as measured from end 446 to end 448, within a range of about 5 mm to about 60 mm, within a range of about 10 mm to about 50 mm, or within a range of about 20 mm to about 40 mm. In particular, cylindrical body 444 may have a length of about 20 mm or about 40 mm. Cylindrical body 444 of implant 440 may have a diameter within a range of about 1.0 mm to about 20 mm, about 1.5 mm to about 15 mm, or about 2 mm to about 10 mm. In particular, a diameter of cylindrical body 444 may be about 2 mm, about 3.5 mm, about 5 mm, about 7 mm, or about 10 mm.

Biomaterials 422, when attached to or incorporated within implant 440, may be provided at different locations throughout cylindrical portion 444. In some aspects, a higher concentration of biomaterials 442 may be provided at distal end 446 and proximal end 448 as compared to an axial center portion of implant 440. Alternatively, biomaterials 402 may be substantially consistently and regularly distributed throughout the entirety of implant 440. In some aspects, biomaterials 402 may include fibers that are oriented in a desired manner. For example, as shown in FIG. 4C, these fibrous biomaterials 442 may extend so as to be generally parallel to each other so as to extend along a circumference of implant 440.

FIG. 4C provides an example where a plurality of biomaterials 442 are formed as fibers that extend generally parallel to each other. Biomaterials 442 may be fibers that extend along a circumference of cylindrical body 444. Additionally or alternatively, implant 440 may include biomaterials 442 that extend in a direction parallel to an axial direction of implant 440. Biomaterials 442 may also extend in differing directions, if desired. Additionally or alternatively, biomaterials 442 may include spirally-extending fibers, and/or other suitable fiber orientations. Any of the other orientations or arrangements, as described with respect to implants 400, 420, and 460, for example, may also be employed in implant 440.

FIG. 4D illustrates an exemplary implant 460 that may be suitable for implantation in a subject. In some aspects, implant 460 may be useful as a nerve graft formed of decellularized material that may be implanted at the site of a peripheral nerve injury in a subject. While implants 400, 420, and 440 may have a hollow interior, implant 460 may include an interior that includes decellularized epineurium, decellularized perineurium, and/or decellularized endoneurium. Biomaterial 462 of implant 460 may generally extend along a length of implant 460, as shown in FIG. 4D. Additionally or alternatively, biomaterial 462 may extend along a circumference of implant 460. Similar to implants 400, 420, and 440, biomaterial 462 may supply a relatively higher concentration at one or more locations, such as proximal and distal ends of implant 460.

Each of the above-described embodiments, including biomaterials 132, 142, 144, 302, 350, 402, 422, 442, and 462, and each of implants 400, 420, 440, and 460, may be configured to deliver agent(s) 110 in a localized, sustained, and controlled manner. For example, it may be desirable to avoid burst release of the one or more neuro-regenerative or immunosuppressive agents, such as rapamycin, in any of the above-described biomaterials and implants. Avoiding a burst release may be desirable, for example, to enable a longer overall duration of rapamycin release and/or to avoid the likelihood of a local concentration exceeding an upper limit of a therapeutic window. Incorporation of rapamycin within a polymer in the manner described herein may enable controlled, sustained release of one or more agent(s) 110, and may avoid undesirable burst release.

While fibrous biomaterials are described above, any suitable form factor or combination of form factors may be employed. In particular, the biomaterial may be provided as fibers, pellets, spheres, springs, or other shapes, either alone or in combination. For example, these biomaterials and implants may enable accurate loading of an active ingredient, such as one or more neuro-regenerative or immunosuppressive agents, into a matrix of a polymer to enable controlled release of the agent(s) when incorporated with other devices or implants. In particular, incorporation of rapamycin within a polymeric delivery system formed with one or more of the above-described biomaterials may allow localized release of rapamycin while axons regenerate toward target end tissue or organs. Local delivery of one or more neuro-regenerative or immunosuppressive agents may be desirable to increase the number of neurons that are able to regenerate their axons, as well as increase the rate of axonal regeneration. The production of a biomaterial containing rapamycin may be useful as a universal or modular delivery system that enables the formation of rapamycin-releasing implants and devices in a plurality of different form factors that are useful in different types of injuries and, in particular, different types of peripheral nerve injuries. The biomaterials described above may also be useful for incorporating an active ingredient, such as one or more neuro-regenerative or immunosuppressive agents, without requiring the addition of these agent(s) after the delivery device (e.g., an implant) has been formed.

One or more of the above-described biomaterials and/or implants may be used together. For example, a fibrous biomaterial (e.g., biomaterial 302) or assembly including a fibrous biomaterial (e.g., biomaterial assembly 350) may be wrapped directly around nerve tissue, and then covered with implant 400, 420, or 440. In such examples, implant 400, 420, or 440 may be free of any active ingredient, such that an entirety of agent(s) 110 at the implantation site are delivered via the implanted biomaterial. Additionally or alternatively, a fibrous biomaterial may be wrapped along a surface and/or adhered to a suitable material, such as one or more layers of SIS, that is implanted independently of implant 400, 420, or 440. The SIS, with an adhesively-attached biomaterial, may secured directly to nerve tissue, or secured to implant 400, 420, 440, as desired.

It should be understood that although the present disclosure has been made with reference to preferred embodiments, exemplary embodiments, and optional features, modifications and variations of the concepts herein disclosed may be resorted to by those skilled in the art, and that such modifications and variations are considered to be within the scope of this disclosure as defined by the appended claims. The specific embodiments and examples provided herein are examples of useful embodiments of the present disclosure and are non-limiting and illustrative only. It will be apparent to one skilled in the art that the present disclosure may be carried out using a large number of variations of the devices, device components, methods, and steps set forth in the present description. As will be recognized by one of skill in the art, methods and devices useful for the present methods can include a large number of various optional compositions and processing elements and steps.

What is claimed is:

1. A method of preparing an implantable biomaterial, comprising:
    combining a polymer with a neuro-regenerative agent or immunosuppressive agent selected from a group comprising at least one of: rapamycin, cyclosporine A, or analogs thereof;
    melting the polymer by heating the polymer, within an extruder, to a temperature within about 150 degrees Celsius to about 250 degrees Celsius; and
    extruding the polymer and the neuro-regenerative agent or immunosuppressive agent to form the implantable biomaterial.

2. The method of claim 1, wherein the neuro-regenerative agent or immunosuppressive agent includes rapamycin and the polymer includes polydioxanone.

3. The method of claim 1, wherein the implantable biomaterial is free of FK506.

4. The method of claim 1, wherein the polymer and the neuro-regenerative agent or immunosuppressive agent are included in one or more pellets.

5. The method of claim 1, wherein the polymer and the neuro-regenerative agent or immunosuppressive agent are included in a fiber.

6. The method of claim 5, wherein the fiber includes one or more knots.

7. The method of claim 5, wherein the fiber has a diameter of about 50 μm to about 600 μm.

8. The method of claim 1, wherein the implantable biomaterial is included in an implant.

9. The method of claim 8, wherein the implant is a nerve wrap.

10. The method of claim 8, wherein the implant is a nerve connector.

11. The method of claim 8, wherein the implant is a pre-rolled nerve wrap.

12. The method of claim 8, wherein the implant is a nerve graft.

13. The method of claim 12, wherein the nerve graft includes decellularized material.

14. The method of claim 1, further including sandwiching the neuro-regenerative agent or immunosuppressive agent between a plurality of layers of small intestine submucosa.

15. The method of claim 1, wherein the temperature within about 150 degrees Celsius to about 250 degrees Celsius is applied to the polymer and to the neuro-regenerative agent or immunosuppressive agent via a shearing section of an extruder screw.

16. The method of claim 1, wherein the temperature for melting the polymer is monitored with a control system of a dual-screw extruder.

17. A method of preparing an implantable biomaterial, comprising:
    combining a polymer with at least one of: rapamycin, cyclosporine A, or analogs thereof;
    melting the polymer;
    in a first extrusion, extruding the combined polymer and the rapamycin with an extruder to form a first biomaterial having a first concentration of the rapamycin; and
    in a second extrusion, extruding the first biomaterial and additional polymer to form the implantable biomaterial with a second concentration of rapamycin.

18. The method of claim 17, wherein the polymer and the at least one of rapamycin, cyclosporine A, or analogs thereof are extruded to form a pellet, a sheet, a spring-shaped biomaterial, or a fiber.

19. The method of claim 17, wherein the polymer is a homopolymer, copolymer, and/or polymeric blend formed by polymerization of one or more of: glycolide, lactide, caprolactone, dioxanone, or trimethylene carbonate, monomers of cellulose derivatives, and monomers that polymerize to form polyesters.

20. The method of claim 17, wherein the polymer is melted for the first extrusion by increasing a temperature of the polymer to within about 150 degrees Celsius to about 250 degrees Celsius at least in part with a shearing section of an extruder screw.

21. The method of claim 20, wherein the temperature of the polymer is monitored with a control system of a dual-screw extruder during the first extrusion.

* * * * *